(12) United States Patent
Moghari et al.

(10) Patent No.: US 10,420,484 B2
(45) Date of Patent: Sep. 24, 2019

(54) SYSTEM AND METHOD FOR MAGNETIC RESONANCE IMAGING WITH AN ADAPTIVE GATING WINDOW HAVING CONSTANT GATING EFFICIENCY

(75) Inventors: Mehdi Hedjazi Moghari, Cambridge, MA (US); Reza Nezafat, Newton, MA (US)

(73) Assignee: Beth Israel Deconess Medical Center, Inc., Boston, MA (US)

( * ) Notice: Subject to any disclaimer, the term of this patent is extended or adjusted under 35 U.S.C. 154(b) by 1798 days.

(21) Appl. No.: 13/372,114

(22) Filed: Feb. 13, 2012

(65) Prior Publication Data

US 2013/0211234 A1   Aug. 15, 2013

(51) Int. Cl.
*A61B 5/05* (2006.01)
*A61B 5/055* (2006.01)
*G01R 33/567* (2006.01)

(52) U.S. Cl.
CPC .......... *A61B 5/055* (2013.01); *G01R 33/5676* (2013.01)

(58) Field of Classification Search
USPC ................................ 600/409–410, 407, 413
See application file for complete search history.

(56) References Cited

U.S. PATENT DOCUMENTS

2003/0214299 A1* 11/2003 Lee et al. ....................... 324/318
2005/0065430 A1* 3/2005 Wiethoff et al. ............... 600/413
2009/0177076 A1* 7/2009 Aldefeld et al. ............... 600/410
2010/0234723 A1* 9/2010 Xu .................................. 600/413
2011/0130644 A1* 6/2011 Stemmer ........................ 600/410

OTHER PUBLICATIONS

Wu et al (Gating based on internal/external signals with dynamic correlation updates, Pys. Med. Biol. 53 (2008) 7137-7150.*
Kolmogorov et al (Simultaneously multiple volume acquisition algorithm for real-time navigator gating, Magnetic Resonance Imaging 21 (2003) 969-975).*
Feinberg et al (Hybrid ultrasound MRI for improved cardiac imaging and real-time respiration control, magnetic resonance in medicine, 2010).*
Finn et al (Cardiac MR imaging, state of the technology, 2006).*
Danias, Prospective Navigator Correction of Image Position for Coronary MR Angiography, Radiology, 1997, 203:733-736.

(Continued)

*Primary Examiner* — Joel F Brutus
(74) *Attorney, Agent, or Firm* — Quarles & Brady LLP

(57) ABSTRACT

A system and method for producing an image of a subject with a magnetic resonance imaging (MRI) system using an adaptive gating window with constant gating efficiency is provided. Navigator data is acquired from the subject and used to produce a gating window having a defined gating efficiency value. Image data is acquired with the MRI system while measuring a position of an anatomical location within the subject. Image data is accepted or rejected based on whether the measured anatomical location is within the gating window. The gating window is updated using the measured position of the anatomical location such that a substantially constant gating efficiency value is maintained. Imaging is repeated with the updated gating window, after which the gating window is again updated. When the desired amount of image data has been acquired, an image of the subject is reconstructed.

14 Claims, 3 Drawing Sheets

(56) References Cited

OTHER PUBLICATIONS

Deshpande, et al., Non-Contrast MR Angiography of the Heart and Great Vessels Using SSFP With Non-Selective Excitation, Proc. Intl. Soc. Mag. Reson. Med., 2006, 14:1935.
Ehman, et al., Adaptive Technique for High-Definition MR Imaging of Moving Structures, Radiology, 1989, 173:255-263.
Huber, et al., Motion Artifact Reduction and Vessel Enhancement for Free-Breathing Navigator-Gated Coronary MRA Using 3D k-space Reordering, Magnetic Resonance in Medicine, 2001, 45(4):645-652.
Jhooti, et al., 3D Coronary Artery Imaging with Phase Reordering for Improved Scan Efficiency, Magnetic Resonance in Medicine, 1999, 41(3):555-562.
Jhooti, et al., Hybrid Ordered Phase Encoding (HOPE): An Improved Approach for Respiratory Artifact Reduction, Journal of Magnetic Resonance Imaging, 1998, 8(4):968-980.
Jhooti, et al., A Fully Automatic and Highly Efficient Navigator Gating Technique for High-Resolution Free-Breathing Acquisitions: Continuously Adaptive Windowing Strategy, Magnetic Resonance in Medicine, 2010, 64(4):1015-1026.
Jhooti, et al., Phase Ordering with Automatic Window Selection (PAWS): A Novel Motion-Resistant Technique for 3D Coronary Imaging, Magnetic Resonance in Medicine, 2000, 43(3):470-480.
Jhooti, et al., Use of Respiratory Biofeedback and CLAWS for Increased Navigator Efficiency for Imaging the Thoracic Aorta, Magnetic Resonance in Medicine, 2011, 66(6):1666-1673.
Kato, et al., Assessment of Coronary Artery Disease Using Magnetic Resonance Coronary Angiography, A National Multicenter Trial, Journal of the American College of Cardiology, 2010, 56(12):983-991.
Kellman, et al., Phase-Sensitive Inversion Recory for Detecting Myocardial Infarction Using Gadolinium-Delayed Hyperenhancement, Magnetic Resonance in Medicine, 2002, 47(2):372-383.
Krishnam, et al., Noncontrast 3D Steady-State Free-Precession Magnetic Resonance Angiography of the Whole Chest Using Nonselective Radiofrequency Excitation Over a Large Field of View: Comparison With Single-Phase 3D Contrast-Enhanced Magnetic Resonance Angiography, Investigative Radiology, 2008, 43(6):411-420.
Look, et al., Time Saving in Measurement of NMR and EPR Relaxation Times, Review of Scientific Instruments, 1970, 41(2):250-251.
McConnell, et al., Prospective Adaptive Navigator Correction for Breath-Hold MR Coronary Angiography, Magnetic Resonance in Medicine, 1997, 37(1):148-152.
McConnell, et al., Comparison of Respiratory Suppression Methods and Navigator Locations for MR Coronary Angiography, AJR, 1997, 168:1369-1375.
McLeish, et al., A Study of the Motion and Deformation of the Heart Due to Respiration, IEEE Transactions on Medical Imaging, 2002, 21(9):1142-1150.
Oshinski, et al., Two-Dimensional Coronary MR Angiography Without Breath Holding, Radiology, 1996, 201:737-743.
Sachs, et al., Real-Time Motion Detection in Spiral MRI Using Navigators, Magnetic Resonance in Medicine, 1994, 32(5):639-645.
Sachs, et al., The Diminishing Variance Algorithm for Real-Time Reduction of Motion Artifacts in MRI, Magnetic Resonance in Medicine, 1995, 34(3):412-422.
Sakuma, et al., Detection of Coronary Artery Stenosis With Whole-Heart Coronary Magnetic Resonance Angiography, Journal of the American College of Cardiology, 2006, 48(10):1946-1950.
Sinkus, et al., Motion Pattern Adapted Real-Time Respiratory Gating, Magnetic Resonance in Medicine, 1999, 41 (1):148-155.
Stuber, et al., Submillimeter Three-Dimensional Coronary MR Angiography with Real-Time Navigator Correction: Comparison of Navigator Locations, Radiology, 1999, 212:579-587.
Stuber, et al., Double-Oblique Free-Breathing High Resolution Three-Dimensional Coronary Magnetic Resonance Angiography, Journal of the American College of Cardiology, 1999, 34(2):524-531.
Wang, et al., Coronary MRI with a Respiratory Feedback Monitor: The 2D Imaging Case, Magnetic Resonance in Medicine, 1995, 33(1):116-121.
Wang, et al., Navigator-Echo-Based Real-Time Respiratory Gating and Triggering for Reduction of Respiration Effects in Three-Dimensional Coronary MR Angiography, Radiology, 1996, 198:55-60.
Wang, et al., Respiratory Motion of the Heart: Kinematics and the Implications for the Spatial Resolution in Coronary Imaging, Magnetic Resonance in Medicine, 1995, 33:713-719.
Weiger, et al., Motion-Adapted Gating Based on k-space Weighting for Reduction of Respiratory Motion Artifacts, Magnetic Resonance in Medicine, 1997, 38(2):322-333.

* cited by examiner

SYSTEM AND METHOD FOR MAGNETIC RESONANCE IMAGING WITH AN ADAPTIVE GATING WINDOW HAVING CONSTANT GATING EFFICIENCY

STATEMENT REGARDING FEDERALLY FUNDED RESEARCH

This invention was made with government support under EB008743 awarded by The National Institutes of Health. The government has certain rights in the invention.

BACKGROUND OF THE INVENTION

The field of the invention relates to systems and methods for magnetic resonance imaging ("MRI"). More particularly, the present invention relates to systems and methods for adaptively gating of MRI acquisitions to allow for free-breathing cardiac MRI acquisitions.

MRI uses the nuclear magnetic resonance ("NMR") phenomenon to produce images. When a substance such as human tissue is subjected to a uniform magnetic field, such as the so-called main magnetic field, $B_0$, of an MRI system, the individual magnetic moments of the nuclei in the tissue attempt to align with this $B_0$ field, but precess about it in random order at their characteristic Larmor frequency, $\omega$. If the substance, or tissue, is subjected to a so-called excitation electromagnetic field, $B_1$, that is in the plane transverse to the $B_0$ field and that has a frequency near the Larmor frequency, the net aligned magnetic moment, referred to as longitudinal magnetization, may be rotated, or "tipped," into the transverse plane to produce a net transverse magnetic moment, referred to as transverse magnetization. A signal is emitted by the excited nuclei or "spins," after the excitation field, $B_1$, is terminated, and this signal may be received and processed to form an image.

When utilizing these "MR" signals to produce images, magnetic field gradients ($G_x$, $G_y$, and $G_z$) are employed for spatial encoding. Typically, the region to be imaged is scanned by a sequence of measurement cycles in which these gradients vary according to the particular localization method being used. The resulting set of received MR signals are digitized and processed to reconstruct the image using one of many well known reconstruction techniques.

Patient motion has been a long-standing challenge to clinical MRI procedures. Patient motion can come in many forms, including bulk and fine motion or voluntary and involuntary motion. Substantial efforts have been made to control or overcome the errors and artifacts introduced by each patient motion.

In the case of involuntary or partially-involuntary motion, diaphragmatic and bellows navigators pulse sequences have been used to allow for the acquisition of free-breathing, three-dimensional cardiovascular MR images with reduced respiratory motion artifacts. The linear relationship between the respiratory motion of the right hemi-diaphragm ("RHD") and the heart allows diaphragmatic navigators to track the RHD motion so that the respiratory motion of the heart can be indirectly corrected.

One method for mitigating patient motion artifacts is referred to as the "accept/reject algorithm." In this method, the location of the RHD is measured during a preparatory phase to determine the location of the RHD at end-expiration. A small gating window, typically with a width of 5-7 mm, is then placed around the end-expiration position. Immediately before each acquisition of k-space lines, the RHD position is again measured. If the RHD position is within the gating window, the acquired k-space lines are accepted for image reconstruction; otherwise, those lines are rejected and reacquired until they are acquired within the gating window. This technique may be used with or without a slice tracking factor to acquire images with sub-millimeter accuracy. While the diaphragmatic navigator successfully suppresses the respiratory motion of the heart, this approach increases the duration of the MRI scan because the rejected k-space lines must be reacquired. Moreover, this approach results in an unpredictable scan acquisition time.

There have been several attempts to improve gating efficiency and reduce scan acquisition time without compromising image quality, including the use of k-space weighting, phase encode reordering, and diminishing variance algorithms. These algorithms reduce the acquisition time, but changes in the patient's breathing pattern can strongly reduce gating efficiency. To mitigate this problem and to maintain a high gating efficiency, an end-expiratory following technique has been proposed to track the position of the RHD at end-expiration and to update the location of the gating window. Although there is no image degradation using this technique compared to the fixed gating window position, the scan time and the range of diaphragm positions in the final image are still unpredictable and can be prolonged.

The other methods have also been proposed as alternatives to the accept/reject algorithm. These include phase ordering with automatic window selection ("PAWS") and continuously adaptive window averaging ("CLAWS"), and were proposed to appropriately account for drifts and variations in breathing patterns. In PAWS and CLAWS, it is assumed that the data acquired at any RHD position may be used to reconstruct the final image; therefore, k-space lines are accepted and reordered using a predetermined algorithm to avoid duplications at different RHD positions. The scan is completed when all k-space lines are acquired within a gating window around an RHD position. These algorithms efficiently complete scans within a gating window in the presence of drifts and variations in breathing pattern, but their scan acquisition times are still long and unpredictable.

Therefore, it would be desirable to have a system and method for mitigating patient motion artifacts in MRI that overcome the limitations of existing methods. Notable limitations include the presence of drifts and variations in a patient's breathing pattern not being accounted for, thereby generating residual motion artifacts. Notable limitations also include unpredictable scan times resulting from no a priori information as to how many repetitions will be required to obtain a complete k-space data set.

SUMMARY OF THE INVENTION

The present invention overcomes the aforementioned drawbacks by providing a system and method for magnetic resonance imaging ("MRI") in the presence of subject motion that use a gating technique in which the size of a gating window is adaptively changed during an imaging scan while maintaining a constant gating efficiency. The adaptive gating window tracks the motion of an anatomical location and changes the size of the gating window based on that motion profile to keep the gating efficiency constant throughout the scan. This adaptive gating with constant gating efficiency allows for completing the scan in a predictable time.

It is an aspect of the invention to provide a method for producing an image of a subject with an MRI system. Navigator data is acquired from the subject with the MRI system, and a gating window having a defined gating efficiency value is produced from the navigator data. Image data is acquired from the subject while measuring a position of an anatomical location within the subject. Image data is stored for reconstruction when the measured position of the anatomical location is within the gating window, and image data is discarding when the measured position of the anatomical location is outside the gating window. The gating window is updated using the measured position of the anatomical location while maintaining a substantially constant gating efficiency of the gating window. Image acquisition and gating window updating is repeated until a desired amount of image data has been acquired, after which an image of the subject is reconstructed from the stored image data.

It is an aspect of the invention to provide an MRI system configured to produce an image of a subject. The MRI system includes a magnet system configured to generate a polarizing magnetic field about at least a portion of a subject arranged in the MRI system, a plurality of gradient coils configured to apply at least one gradient field to the polarizing magnetic field, a radio frequency ("RF") system configured to apply an RF field to the subject and to acquire magnetic resonance ("MR") image data therefrom; and a computer system. The computer system is programmed to direct the MRI system to acquire navigator data from a subject and to produce a gating window having a defined gating efficiency value using the acquired navigator data. The computer system is also programmed to direct the MRI system to acquire image data from the subject while measuring a position of an anatomical location within the subject, and to store the acquired image data for reconstruction when the measured position of the anatomical location is within the gating window or to discard the acquired image data when the measured position of the anatomical location is outside the gating window. The computer system is also programmed to update the gating window using the measured position of the anatomical location while maintaining a substantially constant gating efficiency of the gating window, and to reconstruct an image of the subject from the stored image data.

The foregoing and other advantages of the invention will appear from the following description. In the description, reference is made to the accompanying drawings which form a part hereof, and in which there is shown by way of illustration embodiments of the invention. Such embodiments do not necessarily represent the full scope of the invention, however, and reference is made therefore to the claims and herein for interpreting the scope of the invention.

DESCRIPTION OF THE INVENTION

A respiratory navigator with a fixed acceptance gating window is commonly used to reduce respiratory motion artifacts in cardiac magnetic resonance imaging ("MRI"). This approach prolongs the scan time and occasionally yields an incomplete dataset due to respiratory drifts. To overcome these limitations, a system and method for using an adaptive gating window in which the size of the gating window is changed adaptively during acquisition time based on the individual's breathing pattern is provided. The adaptive gating window tracks the breathing pattern of the subject throughout the scan and adjusts the size of the gating window such that the gating efficiency is always fixed at a constant value. The provided system and method allow free-breathing cardiac MRI in a relatively fixed time without compromising imaging quality due to respiratory motion. It is noted that, while the provided system and method have been described with respect to respiratory motion, it will be appreciated by those skilled in the art that other motion sources can be address with the present invention.

Figure 1:
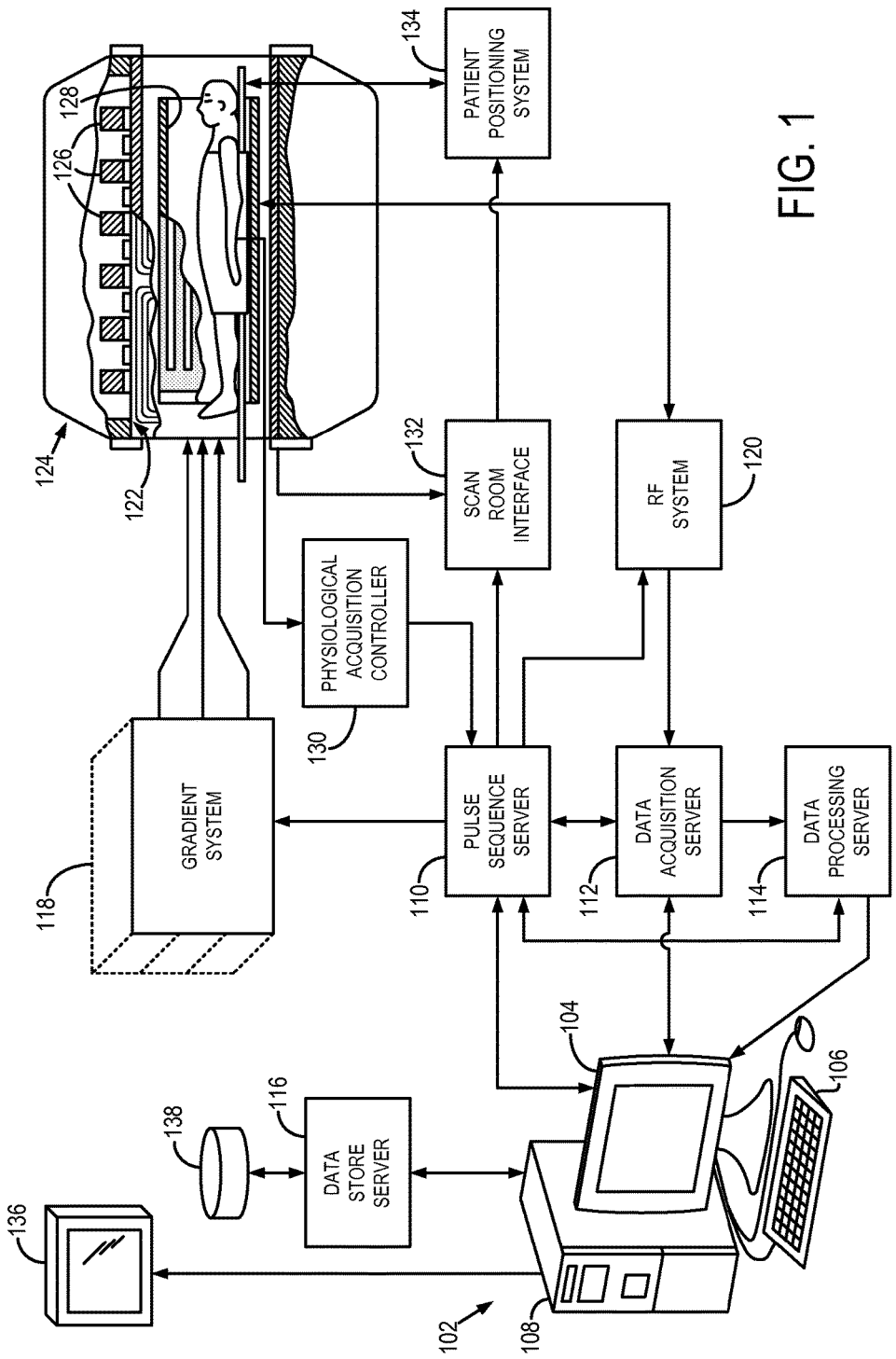
FIG. 1 is a block diagram of an example of a magnetic resonance imaging ("MRI") system for use with the present invention.

Referring particularly now to FIG. 1, an example of an MRI system 100 is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF preamplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \tag{1};$$

and the phase of the received MR signal may also be determined:

$$\varphi = \tan^{-1}\left(\frac{Q}{I}\right). \quad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
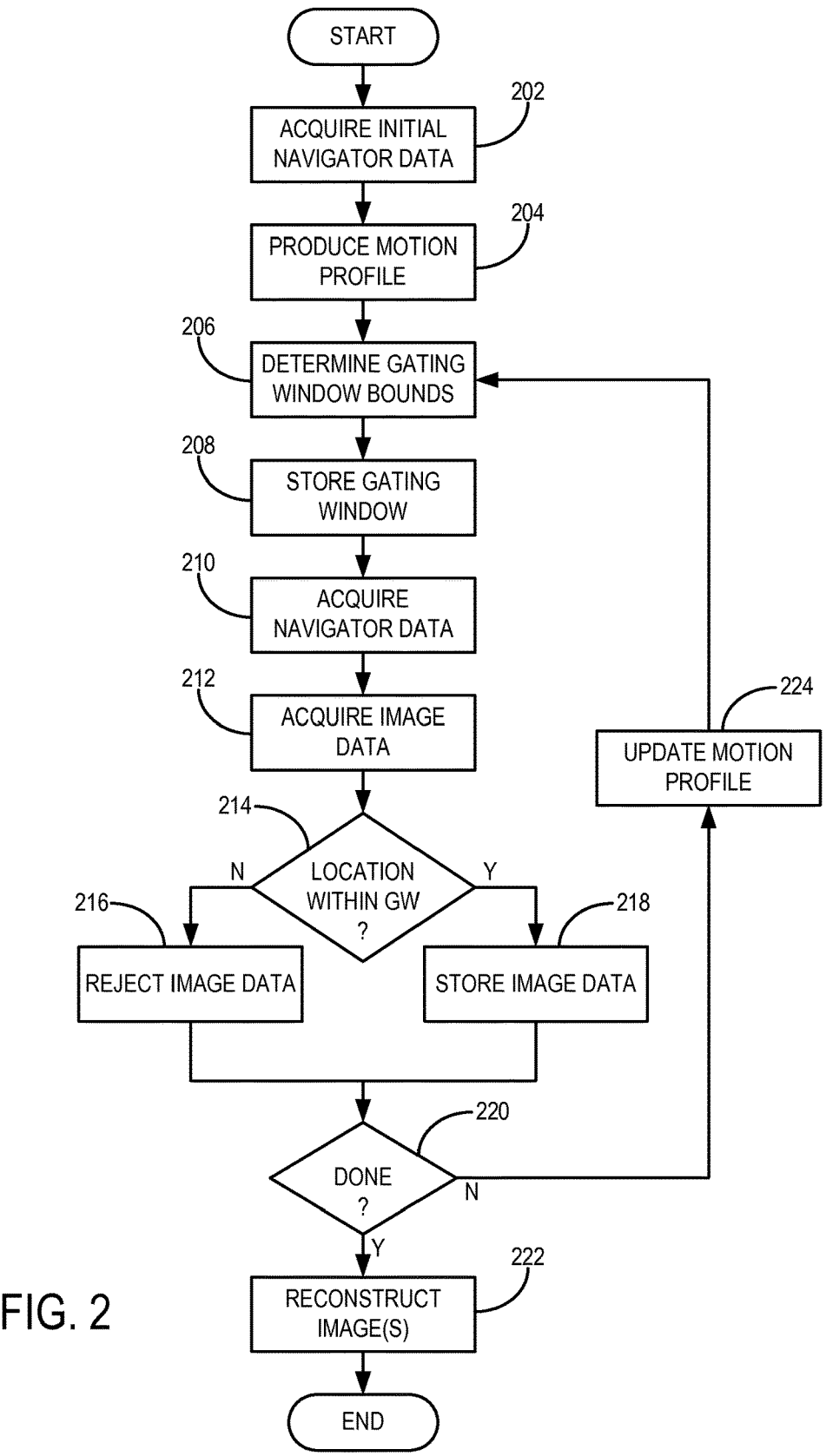
FIG. 2 is a flowchart setting for the steps of an example method for gating a data acquisition with an MRI system using an adaptive gating window with a fixed gating efficiency.

Referring now to FIG. 2, a flowchart setting forth the steps of an example of a method for gating a data acquisition with an MRI system using an adaptive gating window with a fixed gating efficiency is illustrated. The method generally includes a preparation phase and an imaging phase. During the preparation phase, an initial gating window is produced. This initial gating window is adaptively revised during the imaging phase of the method.

Figure 3:
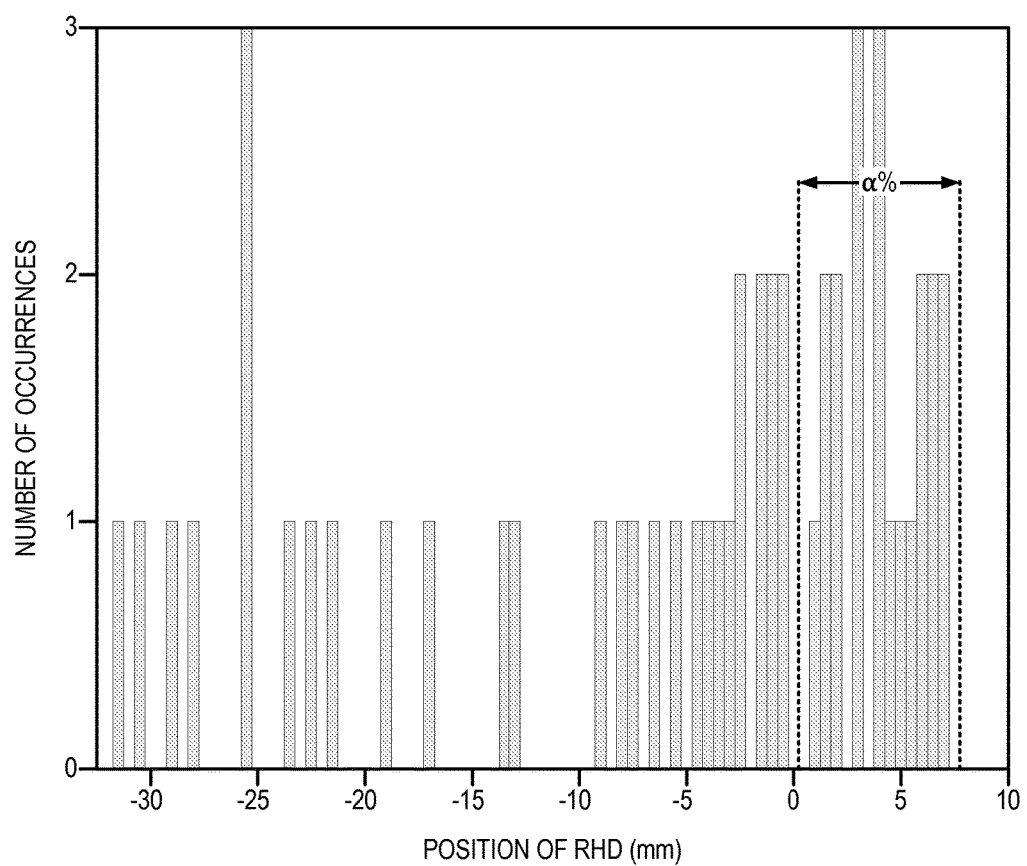
FIG. 3 is an illustration of an example of a motion profile used to determine an adaptive gating window for use with the present invention.

Before the method begins, a user will select an anatomical location to be tracked by a navigator. By way of example, this anatomical location to be tracked may be the dome of the right hemi-diaphragm ("RHD"). It will be appreciated by those skilled in the art, however, that other anatomical locations can be suitably tracked. The method begins with the acquisition of navigator data from the anatomical location, as indicated at step 202. The acquired navigator data includes information pertaining to N samples of the position of the anatomical location. As an example, N may equal fifty samples. Using the acquired navigator data, a motion profile, such as a respiration profile, is produced, as indicated at step 204. The motion profile may be a histogram produced using multiple bins of a preselected size, such as 0.5 mm. A probability distribution function of the anatomical location positions is then calculated by dividing the number of occurrences of anatomical location positions in each bin over the total number of the anatomical location positions, N. An example of a motion profile is illustrated in FIG. 3.

Having produced a motion profile, the adaptive gating window is determined as follows. The upper and lower bounds of the gating window are determined from the motion profile, as indicated at step 206. The upper bound of the gating window may be selected as the maximum position of the anatomical location. For example, when the anatomical location is the RHD, the maximum position will correspond to end-expiration. The lower bound of the gating window is determined from the motion profile and using a preselected gating efficiency parameter, a. As an example, the lower bound is selected as the point where the summation of probabilities between the upper and lower bounds of the gating window is equal to or greater than the preselected gating efficiency value. Because the motion profile is generated from discrete histogram bins, there might not be a lower bound position where the gating efficiency is exactly a percent. In that instance, the first position where the gating efficiency is greater than a percent is chosen for the lower bound of the gating window. The gating window defined by the upper and lower bounds is then stored for use during the imaging phase, as indicated at step 208.

During the imaging phase, navigator data is acquired prior to the acquisition of image data, as indicated at step 210. As will be explained below, this navigator data will be used to measure the position of the anatomical location and used to determine whether to reject the acquired image data. Image data is acquired next, as indicated at step 212. As indicated at decision block 214, a determination is then made as to whether the measured anatomical location is within the gating window. If the anatomical location is within the gating window, the acquired image data are accepted and stored for later image reconstruction, as indicated at step 216; otherwise, the acquired image data are rejected, as indicated at step 218, and reacquired in the next imaging phase.

A determination is then made whether imaging is completed, or whether additional image data should be acquired, as indicated at decision block 220. If imaging is completed, then one or more images are reconstructed from the stored image data, as indicated at step 222. Otherwise, the motion profile is updated, as indicated at step 224, before subsequent imaging. The motion profile is updated as follows. The position of the anatomical location measured from the navigator data acquired during the imaging phase is added to the motion profile and the oldest point in the motion profile is removed from the profile to maintain the number of positions in the motion profile at a constant value of N. Based on the newly anatomical location, the probability distribution of positions is updated. Then, in the repetition of step 206, the upper and lower bounds of the gating window are updated.

The provided adaptive gating window technique can automatically decrease the size of the gating window in subjects with regular breathing patterns who have a high gating efficiency to better gate the respiratory motion and minimize respiratory motion artifacts. Additionally, in subjects with irregular breathing patterns and low gating efficiency, where scans are long and could potentially fail due to drifts, the proposed algorithm automatically increases the gating window size to maintain a constant gating efficiency of a percent and complete the scan. In this case, the mean size of the gating window might be wider than the standard 5-7 mm; therefore, image quality may be compromised, but the scan can be completed in a given time.

Thus, a new adaptive gating window technique using navigators is provided for MRI applications, including free-breathing cardiac MRI. A motion profile, such as a respiration profile that is indicative of a respiration pattern, is used to define the position and the size of a gating window. Furthermore, the gating window is designed to have a substantially constant gating efficiency throughout a scan. During a scan, the proposed algorithm follows the changes in the motion profile and updates the position and the size of the gating window to maintain the gating efficiency at a constant value. Thus, the method completes the scan with a fixed efficiency and in predictable time.

The present invention has been described in terms of one or more preferred embodiments, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for producing an image of a subject with a magnetic resonance imaging (MRI) system, the steps of the method comprising:
   a) acquiring with an MRI system, navigator data from a subject;
   b) producing a gating window having a defined gating efficiency value using the navigator data acquired in step a);
   c) acquiring with the MRI system, image data from the subject while measuring a position of an anatomical location within the subject;
   d) storing the image data acquired in step c) for reconstruction when the position of the anatomical location measured in step c) is within the gating window, and discarding the image data acquired in step c) when the position of the anatomical location measured in step c) is outside the gating window;
   e) updating a size of the gating window using the position of the anatomical location measured in step c) while maintaining a substantially constant gating efficiency of the gating window;
   f) repeating steps c)-e) until a desired amount of image data has been acquired; and
   g) reconstructing an image of the subject from the image data stored in step d).

2. The method as recited in claim 1 in which step b) includes producing from the navigator data acquired in step a), a motion profile indicative of a change in position of the anatomical location within the subject.

3. The method as recited in claim 2 in which step e) includes updating the motion profile using the position of the anatomical location measured in step c).

4. The method as recited in claim 2 in which the gating window is produced by defining an upper bound of the gating window and a lower bound of the gating window using the motion profile.

5. The method as recited in claim 4 in which the upper bound of the gating window is selected as a maximum position of the anatomical location in the motion profile.

6. The method as recited in claim 4 in which the lower bound of the gating window is selected as a point where a sum of probabilities of a position of the anatomical location being in the motion profile between the lower bound and the upper bound is at least one of equal to and greater than the gating efficiency value.

7. The method as recited in claim 1 in which step c) includes acquiring navigator data to measure the position of the anatomical location.

8. The method as recited in claim 1 in which the anatomical location is a right hemi-diaphragm of the subject, and in which the motion profile is a respiration profile indicative of respiratory motion of the subject.

9. A magnetic resonance imaging (MRI) system comprising:
   a magnet system configured to generate a polarizing magnetic field about at least a portion of a subject arranged in the magnet system;
   a plurality of gradient coils configured to apply at least one gradient field to the polarizing magnetic field generated by the magnet system;
   a radio frequency (RF) system configured to apply an RF field to the subject and to acquire magnetic resonance (MR) image data therefrom;
   a computer system programmed to:
      direct the RF system and the plurality of gradient coils to acquire navigator data from a subject;
      produce a gating window having a defined gating efficiency value using the acquired navigator data;
      direct the RF system and the plurality of gradient coils to acquire image data from the subject while measuring a position of an anatomical location within the subject;
      store as stored image data the acquired image data for reconstruction when the measured position of the anatomical location is within the gating window;
      discard the acquired image data when the measured position of the anatomical location is outside the gating window;
      update a size of the gating window using the measured position of the anatomical location while maintaining a substantially constant gating efficiency of the gating window; and
      reconstruct an image of the subject from the stored image data.

10. The MRI system as recited in claim 9 in which the computer system is further programmed to produce the gating window by producing a motion profile indicative of a change in position of the anatomical location within the subject.

11. The MRI system as recited in claim 10 in which the computer system is further programmed to update the gating window by updating the motion profile using the measured position of the anatomical location.

12. The MRI system as recited in claim 10 in which the computer system is further programmed to produce the gating window by defining an upper bound of the gating window and a lower bound of the gating window using the motion profile.

13. The MRI system as recited in claim 12 in which the computer system selects the upper bound of the gating window as a maximum position of the anatomical location in the motion profile.

14. The MRI system as recited in claim 12 in which the computer system selects the lower bound of the gating window as a point in the motion profile where a sum of probabilities of a position of the anatomical location being in the motion profile between the lower bound and the upper bound is at least one of equal to and greater than the gating efficiency value.

* * * * *